United States Patent [19]

Beier et al.

[11] Patent Number: 4,764,513

[45] Date of Patent: Aug. 16, 1988

[54] ANTIGESTAGENS FOR SHIFTING THE ENDOMETRIAL MATURATION

[75] Inventors: Henning M. Beier, Aachen; Walter Elger, Berlin, both of Fed. Rep. of Germany

[73] Assignee: Schering Aktiengesellschaft, Berlin and Bergkamen, Fed. Rep. of Germany

[21] Appl. No.: 907,261

[22] Filed: Sep. 15, 1986

[30] Foreign Application Priority Data

Sep. 13, 1985 [DE] Fed. Rep. of Germany ....... 3533175

[51] Int. Cl.$^4$ ............................................. A61K 31/56
[52] U.S. Cl. ................................................... 514/179
[58] Field of Search .................... 260/397.45; 514/179

[56] References Cited

U.S. PATENT DOCUMENTS

| 4,386,085 | 5/1983 | Teutsch et al. | 260/397.45 |
| 4,589,402 | 5/1986 | Hodgen et al. | 424/100 |
| 4,609,651 | 9/1986 | Rohde et al. | 260/397.45 |

OTHER PUBLICATIONS

Beier, Henning, "The Role of Uterine Proteins in the Establishment of Receptivity of the Uterus", Prog. reprod. Biol., vol. 7, pp. 158–172 (Karger, Base 1980).

*Primary Examiner*—Leonard Schenkman
*Assistant Examiner*—Joseph A. Lipovsky
*Attorney, Agent, or Firm*—Millen & White

[57] ABSTRACT

The endometrial maturation in the post-ovulatory phase (luteal phase) of mammals is delayed with reference to the nidation point by administration of antigestagens.

8 Claims, No Drawings

ANTIGESTAGENS FOR SHIFTING THE ENDOMETRIAL MATURATION

BACKGROUND OF THE INVENTION

This invention relates to the use of antigestagens for shifting the endometrial maturation in the post-ovulatory phase (luteal phase) with reference to the nidation-point.

In recent years, especially in the Western World, a greatly increasing proportion of women find themselves confronted with the problem of undesired sterility. For those women whose sterility is associated with a completely irremovable blockage of the fallopian tubes, a recent gynaecological-embryological technique, first successfully carried out in 1977/1978 by the Britons, Patrick Steptoe and Robert Edwards, has raised hopes for the fulfillment of their desire to bear children. A presupposition of this technique is that at least one of the patient's ovaries as well as her uterus is able to function.

In this process ripe egg-cells are first removed laparoscopically from one of the ovaries and subsequently fertilized in vitro. After the extra-corporeal fertilization, the embryo (zygote) is grown in a culture medium, and then, after about 48 to 72 hours, is implanted in the uterus of the woman.

In this method of therapy of in vitro fertilization and embryo transfer, which now has been used world wide, only a disapointingly small number of human embryos has survived. The main reason for the low number of successes is that the fertilized ova experiences retarded growth in in vitro culture so that a desynchronization occurs between embryo implantation and endometrium maturation.

SUMMARY OF THE INVENTION

It is an object of this invention to provide a method of increasing the survival rate of embryos in the process of in vitro fertilization and embryo transfer.

Another object of this invention is to provide a method of delaying the occurrence of endometrium maturation during the post-ovulatory phase or after removal of an ocyte with reference to the nidation point.

Upon further study of the specification and appended claims, further objects and advantages of this invention will become apparent to those skilled in the art.

Trials with antigestagens have now led to the surprising result that through a "damping" effect of these agents on the "corpus luteum-endometrium" system in the post-ovulatory phase, a delay or a shift forward in time is caused in the pre-implantation phase of the endometrium.

This "damping" effect can be shown experimentally using the prepared rabbit/uteroglobin system. In comparison with other species, the rabbit has the advantage that its luteal phase is analogous to the human and that ovulation and timing of the pre-implantation phase are strictly controllable. (*Prog Reprod Biol*, Vol. 7: "Blastocyst-Endometrium Relationships," Karger, Basel, Muenchen, New York (1980) 158–172).

In this investigation of the rabbit/uteroglobin system it was shown that, after treatment with an effective antigestagen dose, there is a tremendous inhibition of the progesterone-dependent protein, uteroglobin.

Surprisingly however, in the days following such a treatment, the corpus luteum-endometrium system recovers and a uteroglobin secretion is observed. The secretion of uteroglobin corresponds to earlier pre-implantation phases.

By means of this antigestagen treatement, the phase propitious for the implantation of the blastocyst (i.e., receptive phase of the endometrium) can consequently be actively shifted forward in time. Such a "shifting" of the beginning of the luteal phase with reference to the nidation point is only known to be possible with the antigestagen treatment of this invention. Hitherto, neither therapy nor endocrinological measures have been able to cause a shift of the best possible implantation point by influencing the post-ovulatory phase. The retardation of endometrium receptivity for blastocyst implantation caused by administering an effective amount of antigestagen can thus be synchronized with a timely re-transfer of an embryo which has experienced a retarded growth in the in vitro culture.

Thus, it is possible, by means of the antigestagen treatment according to this invention, to achieve a high success rate in such retransfers which previously had no or a lowered chance of a successful implantation due to retarded growth of the embryo in the in vitro culture.

Even a pathological luteal phase (short luteal phase, defective luteal phase) can be favorably influenced with an antigestagen treatment during the period immediately after ovulation. Thus, sterility caused by a defective luteal phase can cdnsequently be treated through the use of antigestagens according to this invention, achieving a delay in accordance with the guidelines given herein.

According to the present invention antigestagens can also be analogously used in veterinary medicine, especially with agriculturally useful animals, such as for example horses, cattle, pigs and sheep. In this usage, the administration of antigestagens can help to achieve a higher success rate in, for example, in vitro fertilization and embryo transfer undertaken for economic or breeding purposes.

According to a preferred mode of operation, the antigestagen treatment, depending on the desired amount of shifting of the endometrial maturation during the luteal phase in a mammal, including humans, as a rule is performed over a period of 1 to 6, and preferably 1 to 4 days, beginning with ovulation and/or the removal of oocytes. The typical length of delay which can be achieved is approx. 3 days. The antigestagen treatment will not be continued after egg transfer. The duration of treatment should correspond to the desired delay of nidation. The antigestagens are used in veterinary medicine in amounts generally of about 0.1 to 20 mg/kg of body weight/day of 11$\beta$-[4-(N,N-dimethylamino)phenyl]-17$\beta$-hydroxy-17$\alpha$-(3-hydroxyprop-1-(Z)-enyl)-4,9(10)-estradien-3-one or a biologically equivalent amount of another antigestagen. For humans, this range is also applicable generically.

For humans the antigestagens are most typically utilized according to the present invention in amounts generally of about 10–200 mg per day, preferably 10–50, of 11$\beta$-[4-(N,N-dimethylamino)phenyl]-17$\beta$-hydroxy-17$\alpha$-(3-hydroxyprop-1-(Z)-enyl)-4,9(10)-estradien-3-one or a biologically equivalent amount of another antigestagen. This activity dose can be determined e.g. by evaluation of the potency to induce premature menstruation in advanced luteal phase of the human cycle as described in e.g. Herrmann, W., Wyss H., Riondel, A. et al Comptes Rendus 294, 933 (1982).

Compounds useful as antigestagens according to the present invention include all compounds which posses a strong affinity for the gestagen receptor (progesterone receptor) and show no gestagen activity of their own. Competitive progesterone antagonists which can be employed are but are not limited to, for example, the following steroids:

11β-[4-(N,N-dimethylamino)phenyl]-17β-hydroxy-17α-propinyl-4,9(10)-estradien-3-one, 11β-[4-(N,N-dimethylamino)phenyl]-17β-hydroxy-18-methyl-17α-propinyl-4,9(10)-estradien-3-one and 11β-[4-(N,N-dimethylamino)phenyl]-17aβ-hydroxy-17aα-propinyl-D-homo-4,9(10)-16-estratrien-3-one (European Patent Application No. 82400025.1 - Publication No. 0 057 115), 11β-methoxyphenyl-17β-hydroxy-17α-ethynyl-4,9(10)-estradien-3-one (Steriods 37 (1981) 361–382), 11β-[4-(N,N-dimethylamino)phenyl]-17β-hydroxy-17α-(3-hydroxyprop-1-(Z)-enyl)-4,9(10)-estradien-3-one (European Patent Application No. 847300147.0 - Publication No. 0 147 361), and 11β-[4-(N,N-dimethylamino)phenyl]-17α-hydroxy-17β-(3-hydroxypropyl)-13α-methyl-4,9(10)-gonadien-3-one (European Patent Application No. 84730062.1 - Publication No. 0 129 499).

The antigestagens can for example be applied locally, topically, enterally or parenterally.

Other useful antigestagens are those disclosed in the aforementioned patent applications.

For the preferred oral administration, particularly suitable are tablets, dragees, capsules, pills, suspensions or solutions which can be prepared in a conventional manner with additives and carriers used in pharmacy. For local or topical application, vaginal pessaries or percutaneous systems such as skin plasters can be used for example. For parenteral application, particularly suitable are solutions, preferably oily or aqueous solutions, as well as suspensions or emulsions. Ampoules are convenient unit dosages.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium sterarate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sertilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilizates obtained, for example, for the preparation of products for injection.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds of a known agent, e.g., by means of an appropriate, conventional pharmacological protocol.

The daily dose of antigestgen can be administered singly or as divided dosages throughout the day. A dosage unit typically contains about 2 to 200 mg of 11β-[4-(N,N-dimethylamino)phenyl]-17β-hydroxy-17α-(3-hydroxyprop-1-(Z)-enyl)-4,9(10)-estradien-3-one or a biologically equivalent amount of another antigestagen.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The following examples illustrate the pharmaceutical formulation of antigestagens.

EXAMPLE 1

Formulation of a tablet with 10 mg of 11β-[4-(N,N-dimethylamino)phenyl]-17β-hydroxy-17α-(3-hydroxyprop-1-(Z)-enyl-4,9(10)-estradien-3-one for oral administration

| | |
|---|---|
| 10.0 mg | 11β-[4,-N,N—dimethylamino)phenyl]-17β-hydroxy-17α-(3-hydroxyprop-1-(Z)-enyl)-4,9(10)-estradien-3-one |
| 140.5 mg | Lactose |
| 69.5 mg | Maize starch |
| 2.5 mg | Polyvinylpyrrolidone 25 |
| 2.0 mg | Aerosil |
| 0.5 mg | Magnesium stearate |
| 225.0 mg | |

EXAMPLE 2

Formulation of an oleaginous solution with 50 mg of 11β-[4-(N,N-dimethylamino)phenyl]-17β-hydroxy-17α-(3-hydroxyprop-1-(Z)-enyl-4,9(10)-estradien-3-one for parenteral administration 50 mg of the antigestagen was dissolved in 1 ml of castor oil/benzyl benzoate, in a ratio by volume of 6:4.

Pharmacological observations

Tests:

A reliable model is available with the uterus-protein secretion of the rabbit endometrium. The synthesis and secretion of the utero-globins in this model is demonstrably progesterone-dependent. Consequently, uteroglobin provides a highly specific marker for progesterone, which can be safely detected in electrophoretic analysis systems. This model, having the progesterone-dependent proteins and the marker protein uteroglobin, is suitable for the investigation and evaluation of the effects of antigestagens.

In a time-dependent study, the antigestagen 11$\beta$-[4-(N,N-dimethylamino)phenyl]-17$\beta$-hydroxy-17$\alpha$-(3-hydroxyprop-1-(Z)-enyl)-4,9(10)-estradien-3-one was studied for (a) its immediate effect after treatment and (b) its long-term effect after completion of the treatment.

Rabbits were put in a state of pseudo-pregnancy by treatment (day 0) with a hCG-injection (150 I.U., i.v.). On day 2, day 3 and day 4, the animals were given an antigestagen treatment with 20 mg/per kg of body weight/per day by stomach probe. On day 5, i.e., 24 hours after termination of the treatment, the uterus protein specimen was electrophoretically analyzed.

Results:

Uteroglobin disappears almost completely from the secretion of the test animals in comparison with both treated control animals, which were given only 1/10th the dosage, and untreated control animals. The altered protein sample of the test animals corresponds to an inhibition of the corpus luteum function.

If the uteroglobin secretion and the usual protein sample are analyzed at later points in time after termination of treatment, there appears surprisingly, a distinct "recovery" from the progesterone inhibition and/or an increasingly marked progesterone activity. At periods of 48 hours, 72 hours and 96 hours after termination of the antigestagen treatment, it is seen that uteroglobin is secreted in a physiological manner, and corresponds to earlier pre-implantation stages. From this it follows, that the antigestagen causes a progesterone inhibition in the corpus luteum and/or in the endometrium in rabbits, which can be characterized as a "damping" or reversible inhibition.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of fertilizing an egg comprising removing an egg from an ovary, fertilizing it in vitro and then implanting it in a uterus of a female, the improvement comprising administering to the female an amount of an antigestagen effective to synchronize the maturation of the endometrium with the implantation of the egg.

2. A method according to claim 1, wherein the antigestagen is administered for a period of 1 to 6 days beginning at the time of removal of an oocyte.

3. A method according to claim 1, wherein the antigestagen is administered for a period of 1 to 4 days beginning at the time of removal of an oocyte.

4. A method according to claim 1, wherein the antigestagen is about 10–200 mg/day of 11$\beta$-[4-(N,N-dimethylamino)phenyl]-17$\beta$-hydroxy-17$\alpha$-(3-hydroxyprop-1-(Z)-enyl)-4,9(10)-estradien-3-one or a biologically equivalent amount of another antigestagen.

5. A method according to claim 1, wherein the antigestagen is about 0.1–20 mg/kg/day of 11$\beta$-[4-(N,N-dimethylamino)phenyl]-17$\beta$-hydroxy-17$\alpha$-(3-hydroxyprop-1-(Z)enyl)-4,9(10)-estradien-3-one or a biologically equivalent amount of another antigestagen.

6. A method according to claim 1, wherein the antigestgen is 11$\beta$-[4-(N,N-dimethylamino)phenyl]-17$\beta$-hydroxy-17$\alpha$-propinyl-4,9(10)-estradien-3-one, 11$\beta$-[4-(N,N-dimethylamino)phenyl]-17$\beta$-hydroxy-18-methyl-17$\alpha$-propinyl-4,9(10)-estradien-3-one, 11$\beta$-[4-(N,N-dimethylamino)-phenyl]-17a$\beta$-hydroxy-17a$\alpha$-propinyl-D-homo-4,9(10)-16-estratrien-3-one, 11$\beta$-methoxyphenyl-17$\beta$-hydroxy-17$\alpha$-ethynyl-4,9(10)-estradien-3-one, 11$\beta$-[4-(N,N-dimethylamino)phenyl]-17$\beta$-hydroxy-17$\alpha$-(3-hydroxyprop-1-(Z)-enyl)-4,9(10)-estradien-3-one or 11$\beta$-[4-(N,N-dimethylamino)phenyl]-17$\alpha$-hydroxy-17$\beta$-(3-hydroxypropyl)-13$\alpha$-methyl-4,9(10)-gonadien-3-one.

7. A method of claim 1 wherein the administration is oral.

8. A method of claim 1 wherein the antigestagen is about 10–200 mg/day of 11$\beta$-[4-(N,N-dimethylamino)phenyl]-17$\beta$-hydroxy-17$\alpha$(3-hydroxyprop-1-(Z)-enyl)-4,9(10)-estradien-3-one.

* * * * *